(12) United States Patent
Lange et al.

(10) Patent No.: US 9,359,570 B2
(45) Date of Patent: Jun. 7, 2016

(54) POLYTETRAHYDROBENZOXAZINES AND BISTETRAHYDROBENZOXAZINES AND USE THEREOF AS A FUEL ADDITIVE OR LUBRICANT ADDITIVE

(71) Applicant: BASF SE, Ludwigshafen (DE)

(72) Inventors: Arno Lange, Bad Duerkheim (DE); Harald Boehnke, Mannheim (DE); Wolfgang Grabarse, Mannheim (DE); Hannah Maria Koenig, Mannheim (DE); Markus Hansch, Speyer (DE); Ludwig Voelkel, Limburgerhof (DE); Ivette Garcia Castro, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/619,171

(22) Filed: Feb. 11, 2015

(65) Prior Publication Data

US 2015/0152349 A1      Jun. 4, 2015

Related U.S. Application Data

(62) Division of application No. 13/313,400, filed on Dec. 7, 2011, now Pat. No. 9,006,158.

(60) Provisional application No. 61/421,226, filed on Dec. 9, 2010.

(51) Int. Cl.

| | |
|---|---|
| *C10L 10/04* | (2006.01) |
| *C10L 1/233* | (2006.01) |
| *C07D 265/16* | (2006.01) |
| *C10L 1/238* | (2006.01) |
| *C10M 133/48* | (2006.01) |
| *C10M 149/14* | (2006.01) |

(52) U.S. Cl.
CPC .............. *C10L 10/04* (2013.01); *C07D 265/16* (2013.01); *C10L 1/233* (2013.01); *C10L 1/238* (2013.01); *C10M 133/48* (2013.01); *C10M 149/14* (2013.01); *C10L 2200/0259* (2013.01); *C10L 2230/22* (2013.01); *C10L 2270/026* (2013.01); *C10M 2215/225* (2013.01); *C10M 2217/041* (2013.01); *C10N 2220/021* (2013.01)

(58) Field of Classification Search
CPC ........ C10L 1/233; C10L 10/04; C07D 265/16
See application file for complete search history.

(56) References Cited

U.S. PATENT DOCUMENTS

| | | | |
|---|---|---|---|
| 2,826,575 A | | 3/1958 | Rigterink |
| 2,826,576 A | | 3/1958 | Rigterink |
| 3,126,290 A | * | 3/1964 | Hemwall et al. ............ 106/632 |
| 4,849,572 A | | 7/1989 | Chen et al. |
| 4,877,416 A | | 10/1989 | Campbell |
| 8,016,898 B1 | | 9/2011 | Lange et al. |
| 2009/0065744 A1 | | 3/2009 | Lange et al. |
| 2010/0263261 A1 | | 10/2010 | Reid |
| 2011/0113678 A1 | | 5/2011 | Lange et al. |
| 2011/0258917 A1 | | 10/2011 | Garcia Castro et al. |
| 2011/0271586 A1 | | 11/2011 | Mähling et al. |

FOREIGN PATENT DOCUMENTS

| | | |
|---|---|---|
| CN | 101041644 A | 9/2007 |
| DE | 38 26 608 A1 | 2/1990 |
| DE | 38 38 918 A1 | 5/1990 |
| DE | 41 42 241 A1 | 6/1993 |
| DE | 43 09 074 A1 | 9/1994 |
| DE | 196 20 262 A1 | 11/1997 |
| DE | 101 02 913 A1 | 7/2002 |
| EP | 0 307 815 A1 | 3/1989 |
| EP | 0 310 875 A1 | 4/1989 |
| EP | 0 356 725 A1 | 3/1990 |
| EP | 0 452 328 | 10/1991 |
| EP | 0 476 485 A1 | 3/1992 |
| EP | 0 548 617 A2 | 6/1993 |
| EP | 0 639 632 A1 | 2/1995 |
| EP | 0 700 985 A1 | 3/1996 |
| EP | 0 831 141 A1 | 3/1998 |
| GB | 24 68 130 A | 9/2010 |
| WO | 87/01126 A1 | 2/1987 |
| WO | 91/03529 A1 | 3/1991 |

(Continued)

OTHER PUBLICATIONS

R.P. Subrayan, et al., "Condensation of substituted phenols with hexakis(methoxymethyl)melamine: synthesis, characterization, and properties of substituted 2,4,6-tris[3,4-dihydro-1,3-(2*H*)-benzoxazin-3-yl]-*s*-triazine derivatives", Chemistry of Materials, vol. 10, No. 11, pp. 3506-3512 (1998).

R. Manikannan, et al., "Synthesis and biological activity of 6-alkyl/chloro-3-{4-(6-alkyl/chloro-2*H*-benzo[e][1,3]oxazin3(4*H*)-yl)phenyl}-3,4-dihydro-2*H*-benzo[e][1,3]oxazines", Indian Journal of Chemistry, vol. 49B, No. 8, XP002667133, pp. 1083-1087 (Aug. 2010).

International Search Report issued Mar. 19, 2012, in PCT/EP2011/071683, filed Dec. 5, 2011 (with translation of Category of Cited Documents).

U.S. Appl. No. 14/436,951, Apr. 20, 2015, Hansch, et al.

*Primary Examiner* — Yong Chu

(74) *Attorney, Agent, or Firm* — Oblon, McClelland, Maier & Neustadt, L.L.P.

(57) ABSTRACT

Polytetrahydrobenzoxazines and bistetrahydrobenzoxazines, obtainable by (A) reacting at least one diamine of the formula $H_2N$-A-$NH_2$ with a $C_1$- to $C_{12}$-aldehyde and a $C_1$- to $C_8$-alkanol at 20 to 80° C. with elimination and removal of water, (B) reacting the condensation product from (A) with a phenol which bears a long-chain substituent at 30 to 120° C., and optionally (C) heating the reaction product from (B) to 125 to 280° C. The resulting polytetrahydrobenzoxazines and bistetrahydrobenzoxazines are suitable as fuel or lubricant additives, especially as detergent additives for diesel fuels.

16 Claims, No Drawings

(56) References Cited

FOREIGN PATENT DOCUMENTS

| | | |
|---|---|---|
| WO | 94/24231 A1 | 10/1994 |
| WO | 96/03367 A1 | 2/1996 |
| WO | 96/03479 A1 | 2/1996 |
| WO | 97/03946 A1 | 2/1997 |
| WO | 00/47698 A1 | 8/2000 |
| WO | 01/25293 A1 | 4/2001 |
| WO | 2007/099048 A2 | 9/2007 |
| WO | 2008/027881 A2 | 3/2008 |
| WO | 2009/040582 A1 | 4/2009 |
| WO | 2009/040583 A1 | 4/2009 |
| WO | 2009/040584 A1 | 4/2009 |
| WO | 2009/040585 A1 | 4/2009 |
| WO | 2011/138400 A1 | 11/2011 |
| WO | 2011/161149 A1 | 12/2011 |
| WO | 2012/004240 A2 | 1/2012 |
| WO | 2012/004300 A1 | 1/2012 |

\* cited by examiner

POLYTETRAHYDROBENZOXAZINES AND BISTETRAHYDROBENZOXAZINES AND USE THEREOF AS A FUEL ADDITIVE OR LUBRICANT ADDITIVE

This application is a divisional of U.S. application Ser. No. 13/313,400 filed Dec. 7, 2011 (now issued as U.S. Pat. No. 9,006,158), which is non-provisional of 61/421,226 filed Dec. 9, 2010, both of which are incorporated herein by reference.

The present invention relates to novel polytetrahydrobenzoxazines which can be defined by the preparation process specified below or alternatively by the general structural formula I specified below. The polytetrahydrobenzoxazines may also be present in quaternized form.

The present invention further relates to novel bistetrahydrobenzoxazines which occur as intermediates in the preparation of the polytetrahydrobenzoxazines.

The present invention further relates to the use of the polytetrahydrobenzoxazines and of the bistetrahydrobenzoxazines as a fuel additive or lubricant additive, especially as a detergent additive for diesel fuels, in particular for direct-injection diesel engines, and to additive concentrates, fuel compositions and lubricant compositions which comprise the polytetrahydrobenzoxazines or bistetrahydrobenzoxazines.

In direct-injection diesel engines, the fuel is injected and distributed ultrafinely (nebulized) by a multihole injection nozzle which reaches directly into the combustion chamber in the engine, instead of being introduced into a prechamber or swirl chamber as in the case of the conventional (chamber) diesel engine. The advantage of the direct-injection diesel engines lies in their high performance for diesel engines and a nevertheless low fuel consumption. Moreover, these engines achieve a very high torque even at low speeds.

At present, essentially three methods are being used to inject the fuel directly into the combustion chamber of the diesel engine: the conventional distributor injection pump, the pump-nozzle system (unit-injector system or unit-pump system) and the common-rail system.

In the common-rail system, the diesel fuel is conveyed by a pump with pressures up to 2000 bar into a high-pressure line, the common rail. Proceeding from the common rail, branch lines run to the different injectors which inject the fuel directly into the combustion chamber. The full pressure is always applied to the common rail, which enables multiple injection or a specific injection form. In the other injection systems, in contrast, only lesser variation of injection is possible. The injection in the common rail is divided essentially into three groups: (1.) pre-injection, by which essentially softer combustion is achieved, such that hard combustion noises ("nailing") are reduced and the engine appears to run quietly; (2.) main injection, which is responsible especially for a good torque profile; and (3.) post-injection, which especially ensures a low nitrogen oxide value in the exhaust gas. In this post-injection, the fuel is generally not combusted, but instead evaporated by residual heat in the cylinder. The exhaust gas/fuel mixture formed is transported to the exhaust gas system, where the fuel, in the presence of suitable catalysts, acts as a reducing agent for the nitrogen oxides.

The variable, cylinder-individual injection in the common-rail injection system can positively influence the pollutant emission of the engine, for example the emission of nitrogen oxides ($NO_x$), carbon monoxide (CO) and especially of particulates (soot). This makes it possible, for example, that engines equipped with common-rail injection systems can meet the Euro 4 standard theoretically even without additional particulate filters.

In modern common-rail diesel engines, under particular conditions, for example when biodiesel-containing fuels or fuels with metal impurities such as zinc compounds, copper compounds, lead compounds and further metal compounds are used, deposits can form on the injector orifices, which adversely affect the injection performance of the fuel and hence impair the performance of the engine, i.e. especially reduce the power, but in some cases also worsen the combustion. The formation of deposits is enhanced further by further developments of the injector construction, especially by the change in the geometry of the nozzles (narrower, conical orifices with rounded outlet). For lasting optimal functioning of engine and injectors, such deposits in the nozzle orifices must be prevented or reduced by suitable fuel additives.

WO 2009/040582 describes the use of a Mannich reaction product of an aldehyde, a polyamine and a substituted phenol with a substituent which has a mean molecular weight of less than 300 as a diesel additive for improving the efficiency of the diesel engine, especially reducing the power loss in the engine and reducing the level of deposits on the injectors.

WO 2009/040583 describes the use of the combination of a Mannich reaction product of an aldehyde, a polyamine and a substituted phenol with a polyisobutylsuccinimide as a diesel additive for improving the efficiency of the diesel engine, especially reducing the power loss in the engine and reducing the level of deposits on the injectors.

WO 2009/040584 describes a metal-containing diesel fuel which, as an efficiency-improving additive, comprises a Mannich reaction product of an aldehyde, a polyamine of the structure of an optionally substituted ethylenediamine and a substituted phenol. The improvement in efficiency consists especially in the reduction in the power loss in the engine, the reduction in the level of deposits on the injectors, the reduction in the level of deposits in the fuel filter, and the reduction of fuel consumption.

WO 2009/040585 describes the use of a Mannich reaction product of an aldehyde, a polyamine and a substituted phenol, where the molar ratio of phenol to polyamine in the reaction mixture is at least 1.5:1, as a diesel additive for improving the efficiency of the diesel engine, especially reducing the power loss in the engine, reducing the level of deposits on the injectors, reducing the level of deposits in the fuel filter and reducing fuel consumption.

GB-A 2 468 130 discloses a diesel fuel which comprises one or more efficiency-enhancing additives from the group of the polymeric or nonpolymeric phenol-ammonia-aldehyde Mannich adducts, the polyisobutylsuccinimides, the antioxidants, the mixtures of polyisobutylsuccinimides with polyether carrier oils and the phenol-polyamine-aldehyde Mannich adducts. These additives bring about an improvement in the efficiency of the diesel engine and a reduction in the level of deposits in the diesel engine.

WO 2008/027881 describes quaternary ammonium salts as reaction products of Mannich adducts which have a tertiary amino group and are obtainable from a substituted phenol, an aldehyde and an amine, and a quaternizing agent. These quaternary ammonium salts are suitable inter alia as additives in fuels.

However, the additive systems described in the prior art have a series of disadvantages—especially in the case of direct-injection diesel engines, in particular in those with common-rail injection systems. Excessive deposits still occur in the injection systems of the engines, and the fuel consumption and the power loss are still too high. Furthermore, the diesel fuels additized with the additive systems described in the prior art still have low-temperature properties which are in need of improvement. The compatibility of motor oils with the additive systems described in the prior art is also still not optimal.

It is therefore an object of the present invention to provide fuel and lubricant additives with improved efficiency. The object is achieved by the polytetrahydrobenzoxazines and bistetrahydrobenzoxazines described hereinafter.

The inventive polytetrahydrobenzoxazines can be defined by the process for preparing them. Accordingly, the present invention provides polytetrahydrobenzoxazines which are obtainable by the reaction steps of (A) reacting at least one diamine of the general formula $H_2N$-A-$NH_2$, in which the bridging member A is $C_1$- to $C_{20}$-alkylene which may be interrupted by up to 10 oxygen atoms and/or tertiary nitrogen atoms, $C_2$- to $C_{20}$-alkenylene, $C_5$- to $C_{20}$-cycloalkylene, $C_6$- to $C_{20}$-arylene or $C_7$- to $C_{20}$-aralkylene with at least one $C_1$- to $C_{12}$-aldehyde and at least one $C_1$- to $C_8$-alkanol at a temperature of 20 to 80° C. with elimination and removal of water, where both the aldehyde and the alcohol may be used in each case in more than double the molar amount compared to the diamine;

(B) reacting the condensation product from reaction step (A) with at least one phenol which bears at least one long-chain substituent having 6 to 30 carbon atoms in a stoichiometric ratio to the diamine originally used in step (A) of 1.2:1 to 3.5:1 at a temperature of 30 to 120° C.;

(C) heating the reaction product from reaction step (B) to a temperature of 125 to 280° C. for at least 10 minutes.

$C_1$- to $C_{20}$-alkylene for the bridging member A represents linear or mono- or polybranched saturated hydrocarbon bridging members having 1 to 20, especially 1 to 10 and in particular 1 to 4 carbon atoms, for example —$CH_2$—, —$(CH_2)_2$—, —$CH(CH_3)$—, —$(CH_2)_3$—, —$CH_2$—CH($CH_3$)—, —$(CH_2)_4$—, —$CH_2CH_2$—$CH(CH_3)$—, —$CH_2$—$CH(CH_3)$—$CH_2$—, —$(CH_2)_5$—, —$CH_2$—$C(CH_3)_2$—$CH_2$—, —$(CH_2)_6$—, —$CH(CH_3)$—$(CH_2)_2$—$CH(CH_3)$—, —$CH(CH_3)$—$(CH_2)_3$—$CH(CH_3)$—, —$(CH_2)_7$— or —$(CH_2)_8$—.

In the case of an interruption of the $C_1$- to $C_{20}$-alkylene bridging member by up to 10, especially by up to 4 and in particular by one or two or three oxygen atoms and/or tertiary nitrogen atoms, the following are examples of possible structures for A: —$CH_2$—O—$CH_2$—, —$CH_2CH_2$—O—$CH_2CH_2$—, —$CH_2$—O—$CH_2CH_2$—O—$CH_2$—, —$CH_2$—O—$CH_2CH_2$—O—$CH_2CH_2$—O—$CH_2$—, —$CH_2CH_2$—O—$CH_2CH_2$—, —$CH_2CH_2$—O—$CH_2CH_2$—O—$CH_2CH_2$—, $CH_2$—N($CH_3$)—$CH_2$— or —$CH_2CH_2$—N($CH_3$)—$CH_2CH_2$—. The side chains on interrupting tertiary nitrogen atoms are typically $C_1$- to $C_4$-alkyl radicals such as methyl or ethyl; in the case of occurrence of such tertiary nitrogen atoms, the maximum carbon number of 20, especially of 10 and in particular of 4 is not exceeded even including the alkyl side chains.

$C_2$- to $C_{20}$-alkenylene for the bridging member A represents mono- or polyunsaturated, especially mono unsaturated, hydrocarbon bridging members having 1 to 20, especially 1 to 10 and in particular 1 to 4 carbon atoms, for example —CH=CH—, —CH=CH—$CH_2$—, —CH=CH—$CH_2$—$CH_2$—, —$CH_2$—CH=CH—$CH_2$—, —CH=CH—CH=CH—, —$CH(CH_3)$—CH=CH— or —$CH_2$—$C(CH_3)$=CH—.

$C_5$- to $C_{20}$-cycloalkylene, especially $C_5$- to $C_8$-cycloalkylene, for the bridging member A is, for example, 1,1-, 1,2- or 1,3-cyclopentylene, 1,1-, 1,2-, 1,3- or 1,4-cyclohexylene, 1,1-, 1,2-, 1,3- or 1,4-cycloheptylene or 1,1-, 1,2-, 1,3-, 1,4- or 1,5-cyclooctylene, which may additionally bear one or more $C_1$- to $C_4$-alkyl substituents such as methyl or ethyl groups, or is a dicyclohexylmethane skeleton with free valences in the 4 and 4' positions on the cyclohexyl rings.

$C_6$- to $C_{20}$-arylene, especially $C_6$- to $C_{14}$-arylene, for the bridging member A is, for example, ortho-, meta- or para-phenylene, naphthylenes, anthracylenes, phenan-thrylenes or 4,4'-diphenylene, which may additionally bear one or more $C_1$- to $C_4$-alkyl substituents such as methyl or ethyl groups on their aromatic rings.

$C_7$- to $C_{20}$-aralkylene, especially $C_7$- to $C_{12}$-aralkylene, for the bridging member A represents structures with one free valence originating from an $sp^2$-hybridized carbon atom in an aromatic ring and with the other free valence originating from an $sp^3$-hybridized carbon atom in a size chain of the aromatic ring such as a phenyl ring, or with both free valences originating from $sp^3$-hybridized carbon atoms in different side chains of an aromatic ring, for example ortho-, meta- or para-$C_6H_4$—$CH_2$—, ortho-, meta- or para-$C_8H_4$—$CH_2CH_2$—, ortho-, meta- or para-$C_6H_4$—$(CH_2)_3$—, ortho-, meta- or para-$C_6H_4$—$(CH_2)_4$— or ortho-, meta- or para-$CH_2$—$C_6H_4$—$CH_2$—.

In a preferred embodiment, the inventive polytetrahydrobenzoxazines are obtainable in reaction step (A) from at least one diamine of the general formula $H_2N$—$(CH_2)_x$—$NH_2$ [i.e. A=—$(CH_2)_x$—], in which x is a number from 1 to 10. Particular preference is given to diamines of the general formula $H_2N$—$(CH_2)_x$—$NH_2$, in which x is a number from 1 to 8, especially a number from 1 to 4, in particular the number 2. When x=2, said diamine is 1,2-ethylenediamine.

Suitable $C_1$- to $C_{12}$-aldehydes, especially $C_1$- to $C_7$-aldehydes, are, for example, formaldehyde, acetaldehyde, propionaldehyde, butyraldehyde, valeraldehyde or benzaldehyde. In a preferred embodiment, the inventive polytetrahydrobenzoxazines are obtainable in reaction step (A) from formaldehyde or a polymeric form of formaldehyde, such as paraformaldehyde or 1,3,5-trioxane.

Suitable $C_1$- to $C_8$-alkanols, especially $C_1$- to $C_4$-alkanols, are, for example, methanol, ethanol, n-propanol, isopropanol, n-butanol, sec-butanol, isobutanol, tert-butanol, n-pentanol, sec-pentanol, isopentanol, tert-pentanol, n-hexanol, n-heptanol, n-octanol, 2-ethylhexanol, n-nonanol, isononanol or n-decanol, and also mixtures of such alkanols. In a preferred embodiment, the inventive polytetrahydrobenzoxazines are obtainable in reaction step (A) from at least one $C_3$- or $C_4$-alkanol.

The diamine of the formula $H_2N$-A-$NH_2$ is reacted with the $C_1$- to $C_{12}$-aldehyde and the $C_1$- to $C_8$-alkanol generally at room temperature to slightly elevated temperature, i.e. at 20 to 80° C., especially at 25 to 70° C. and in particular at 30 to 60° C. Preference is given to working under gentle vacuum, i.e. at 20 mbar to standard pressure, especially at 30 to 700 mbar, in particular at 40 to 500 mbar, in order to be able to better remove the water eliminated from the reaction mixture—for example by azeotropic distillation. The optimal temperature and pressure settings depend of course on the boiling point of the $C_1$- to $C_8$-alkanol(s) used. The preferred ranges specified above for temperature and pressure settings are particularly recommended in the case of use of $C_3$- or $C_4$-alkanols.

The diamine of the formula $H_2N$-A-$NH_2$ is reacted with the $C_1$- to $C_{12}$-aldehyde and the $C_1$- to $C_8$-alkanol advantageously in an inert organic solvent or a mixture of such solvents, especially a hydrocarbon such as hexane, cyclohexane, toluene or xylene, or a halohydrocarbon such as chloroform or chloroform or chlorobenzene. In many cases, it has been found to be advantageous first to initially charge the $C_1$- to $C_{12}$-aldehyde and the $C_1$- to $C_8$-alkanol at room temperature or very low temperature in the inert solvent, then to add the diamine and then—optionally under reduced pressure—to heat to reaction temperature and to remove the water eliminated. The reaction time is typically 1 to 10 hours.

mixture are typically in chemical equilibrium with one another, such that normally all or almost all components of this mixture are available for further reaction in the next reaction step, (B), for the purposes of the present invention.

Such a mixture, which is obtainable, for example, by reacting ethylenediamine, formaldehyde and isobutanol, is represented below by way of example with its components:

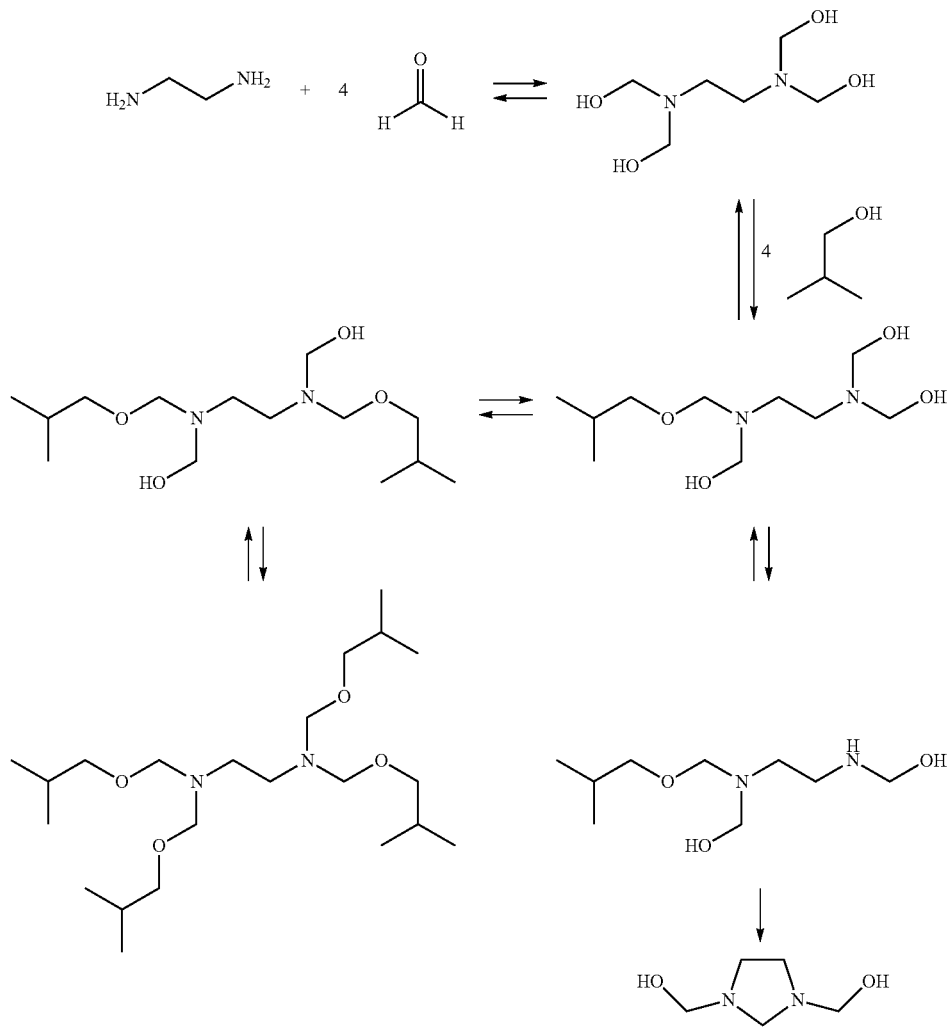

In a preferred embodiment, the stoichiometric ratio of diamine to aldehyde in reaction step (A) is 1:4, where a deviation from this ratio of up to 10% can be tolerated, and the alkanol is used in at least 3.5 times the molar amount, especially 4 times the molar amount, compared to the diamine. The alcohol can also be used in a higher amount, i.e. in excess, for example in 4 to 8 times the molar amount compared to the diamine. The preferred stoichiometric ratio of diamine to aldehyde is thus typically in the range of 1:(3.6-4.4) or of (0.9-1.1):4, especially of 1:(3.9-4.1) or of (0.97-1.03):4.

In reaction step (A), the active agent for the reaction with the phenol is obtained in reaction step (B), which is generally a mixture of the partly or fully hydroxyalkylated diamine which is in partly or fully etherified form with the $C_1$- to $C_8$-alkanol, and possibly ring-closed conversion products such as imidazolidines. The individual components of this The phenol used in reaction step (B) bears, as the at least one long-chain substituent having 6 to 3000 carbon atoms, typically a corresponding hydrocarbyl radical. A hydrocarbyl radical shall be understood here to mean a hydrocarbon radical of any structure which, however, in a minor amount, may also comprise heteroatoms such as oxygen atoms and/or nitrogen atoms and/or halogen atoms, and/or may bear functional groups such as hydroxyl groups, carboxyl groups, carboxylic ester groups, cyano groups, nitro groups and/or sulfo groups. Said long-chain hydrocarbyl radical may be saturated or unsaturated in nature; it may have a linear or branched structure; it may comprise aromatic and/or heterocyclic substructures. The at least one long-chain substituent on the phenol serves principally to make the inventive polytetrahydrobenzoxazines better soluble in mineral oil products such as fuels and lubricants.

This relatively long-chain hydrocarbyl radical on the phenol is preferably a hydrocarbyl radical having 6 to 30 carbon atoms or a polyisobutyl radical having 16 to 3000 carbon atoms.

Useful hydrocarbyl radicals having 6 to 30 carbon atoms on the phenol are preferably $C_6$- to $C_{30}$-alkenyl radicals, especially $C_7$- to $C_{20}$-alkenyl radicals, in particular $C_8$- to $C_{18}$-alkenyl radicals and very especially $C_6$- to $C_{30}$-alkyl radicals, especially $C_7$- to $C_{18}$-alkyl radicals, and in particular $C_8$- to $C_{12}$-alkyl radicals. The phenol may bear one, two or three such long-chain substituents; the phenol preferably bears one such long-chain substituent. In addition to the long-chain substituents, the phenol may also bear one, two or three shorter-chain alkyl or alkenyl radicals such as methyl, ethyl, n-propyl, isopropyl, n-butyl, sec-butyl, isobutyl, tert-butyl, vinyl or allyl radicals, and/or one, two or three functional groups such as halogen atoms, for example chlorine or bromine, nitro groups, cyano groups, carboxyl groups, carboxylic ester groups or sulfo groups, where the total number of substituents on the phenol is not more than 5, preferably not more than 4 and in particular not more than 3.

Examples of said phenols having at least one long-chain substituent having 6 to 30 carbon atoms are phenols with an n-hexyl, n-heptyl, n-octyl, tert-octyl, 2-ethylhexyl, n-nonyl, isononyl, n-decyl, 2-propylheptyl, n-undecyl, n-dodecyl, n-tridecyl, isotridecyl, n-tetradecyl, n-hexadecyl, n-octadecyl, oleyl, linolyl or linolenyl radical in the ortho or para position, and also ortho-cresol having one of the abovementioned long-chain alkyl or alkenyl radicals in the 4 or 6 position, meta-cresol having one of the abovementioned long-chain alkyl or alkenyl radicals in the 4 or 6 position, para-cresol having one of the abovementioned long-chain alkyl or alkenyl radicals in the 2 or 6 position, and phenols having two identical or different abovementioned long-chain alkyl or alkenyl radicals in the 2 and 4 position.

In the case of polyisobutyl radicals, these comprise preferably 21 to 1000, especially 26 to 3000 or especially 26 to 500, in particular 30 to 3000 or in particular 30 to 250 carbon atoms, or they have number-average molecular weights $M_n$ of 183 to 42 000, preferably 500 to 15 000, especially 700 to 7000, in particular 900 to 3000, most preferably 900 to 1100.

The phenol may bear one, two or three such polyisobutyl radicals; the phenol preferably bears one such polyisobutyl radical. In addition to the polyisobutyl radicals, the phenol may also bear one, two or three shorter-chain hydrocarbyl radicals such as methyl, ethyl, n-propyl, isopropyl, n-butyl, sec-butyl, isobutyl, tert-butyl, vinyl, allyl-, n-pentyl, sec-pentyl, isopentyl, tert-pentyl, n-hexyl, n-heptyl, n-octyl, tert-octyl-, 2-ethylhexyl, n-nonyl, isononyl, n-decyl, 2-propylheptyl, n-undecyl, n-dodecyl, n-tridecyl, isotridecyl, n-tetradecyl, n-hexadecyl, n-octadecyl, oleyl, linolyl or linolenyl radicals and/or one, two or three functional groups such as halogen atoms, for example chlorine or bromine, nitro groups, cyano groups, carboxyl groups, carboxylic ester groups or sulfo groups, where the total number of substituents on the phenol is not more than 5, preferably not more than 4 and in particular not more than 3.

In a preferred embodiment, the inventive polytetrahydrobenzoxazines are obtainable in reaction step (B) from at least one phenol which bears, in the para position (4 position) to the hydroxyl group, a $C_8$- to $C_{12}$-alkyl radical or a polyisobutyl radical having 16 to 3000 carbon atoms.

The reaction of the condensation product from reaction step (A) with the at least one long-chain-substituted phenol is effected in reaction step (B) at higher temperatures than in reaction step (A), i.e. at 30 to 120° C., especially at 35 to 105° C., in particular at 40 to 90° C. Preference is given to working at standard pressure. The reaction is effected advantageously in an inert organic solvent or a mixture of such solvent, especially an aromatic hydrocarbon such as toluene, xylene or a technical mixture of relatively high-boiling aromatic hydrocarbons, for example Solvesso™ 100, 150, 200, 150 ND or 200 ND. The reaction time is typically 1 to 10 hours. The stoichiometric ratio of phenol to diamine used in reaction step (A) is preferably 1.5:1 to 3.0:1, especially 1.75:1 to 2.75:1, in particular 1.9:1 to 2.6:1.

The product obtained in reaction step (B) has, or has predominantly, the structure of a bistetrahydrobenzoxazine of the general formula II

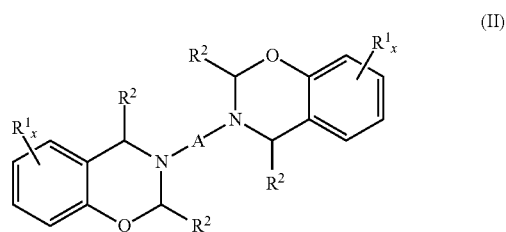

(II)

in which
x is the number 1, 2 or 3,
$R^1$ denotes identical or different $C_1$- to $C_{3000}$-hydrocarbyl radicals, where each benzene ring bears at least one $C_6$- to $C_{3000}$-hydrocarbyl radical,
$R^2$ denotes hydrogen or identical or different $C_1$- to $C_{11}$-alkyl radicals, and
A is a bridging member having 1 to 20 carbon atoms, and ring-opened forms of the bistetrahydrobenzoxazines of the general formula II resulting from hydrolysis of one or both tetrahydrooxazine rings, where $R^1$ are the substituents of the phenol used, $R^2$ is the radical of the aldehyde used, and A corresponds to the bridging member A in the general formula for the diamine $H_2N$-A-$NH_2$.

In the compounds II, it is also possible for different $R^1$ substituents to occur when mixtures of different phenols are used in reaction step (B).

A typical example of a bistetrahydrobenzoxazine of the general formula II is the compound of the formula IIa reproduced below:

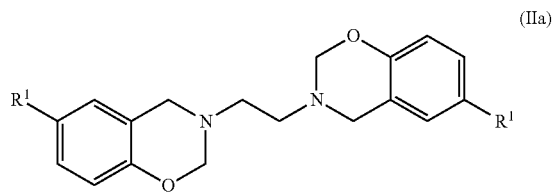

(IIa)

in which $R^1$ is, for example, tert-octyl, n-nonyl, n-dodecyl or polyisobutyl having an $M_n$ of 1000.

Reaction step (C) is undertaken by heating the reaction product from reaction step (B) to temperatures distinctly above those of step (B). Preference is given here to working at 150 to 250° C., especially at 175 to 230° C., in particular at 190 to 220° C., and preferably at standard pressure. The heating to the temperature range specified is effected for at least 10 minutes, preferably for at least 30 minutes, in particular for 45 to 120 minutes. The bistetrahydrobenzoxazines II polymerize essentially with opening of tetrahydrooxazine rings and form a highly branched—but not crosslinked to the extent that it is sparingly soluble or insoluble in mineral oil media—two- to three-dimensional polymer system.

The heating of the reaction product from reaction step (B) is effected in reaction step (C) advantageously in an inert organic solvent or a mixture of such solvents, especially an aromatic hydrocarbon such as toluene, xylene or a technical mixture of higher-boiling aromatic hydrocarbons, for example Solvesso™ 100, 150, 200, 150 ND or 200 ND.

A typical example of a polytetrahydrobenzoxazine formed in reaction step (C) is reproduced below as the compound of the general formula Ia:

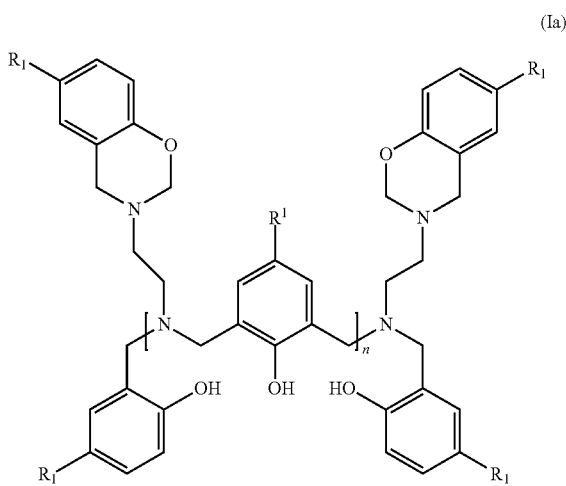

The substituents $R^1$ are each as defined above; it is also possible for different substituents $R^1$ to occur in the molecule when mixtures of different phenols are used in reaction step (B). The serial number n typically assumes values of 2 to 10, especially 4 to 8.

In the inventive polytetrahydrobenzoxazines, the ends of the side chains usually still consist of closed tetrahydrooxazine rings. As a result of hydrolysis of some or all tetrahydrobenzoxazine rings still present in the end product, the inventive polytetrahydrobenzoxazines may, however, also have ring-opened forms. Whether such a hydrolytic ring opening occurs depends substantially on the boundary conditions of the polymerization in reaction step (C)—for example the moisture content and the presence of compounds with catalytic ring-opening action, such as protons or Lewis acids.

The inventive polytetrahydrobenzoxazines preferably have a number-average molecular weight ($M_n$) of 700 to 50 000, especially of 1500 to 25 000, in particular of 2500 to 10 000, and a polydispersity index (PDI) of 1.5 to 7.5, preferably of 2.0 to 5.0.

To modify or improve the efficacy as fuel or lubricant additives, the polytetrahydrobenzoxazines described can be subsequently quaternized. Therefore, the present invention also provides quaternized polytetrahydrobenzoxazines which are obtainable by the reaction steps (A), (B) and (C) described, and additionally the reaction step (D) quaternizing some or all quaternizable amino functions of the reaction product from reaction step (C).

The quaternizable amino functions in the polytetrahydrobenzoxazines described are the tertiary nitrogen atoms.

Useful quaternizing agents are in principle all compounds suitable as such. In a preferred embodiment, the inventive quaternized polytetrahydrobenzoxazines are obtainable in reaction step (D) by quaternizing with at least one epoxide.

This epoxide is preferably a hydrocarbyl epoxide whose four substitutents are the same or different and are each hydrogen or hydrocarbyl radicals, where the hydrocarbyl radicals each have 1 to 10 carbon atoms and at least one such hydrocarbyl radical must be present. More particularly, these are aliphatic or aromatic radicals, for example linear or branched $C_1$- to $C_{10}$-alkyl radicals, or aromatic radicals such as phenyl or $C_1$- to $C_4$-alkylphenyl.

Suitable such hydrocarbyl epoxides are, for example, aliphatic and aromatic alkylene oxides, such as especially $C_2$- to $C_{12}$-alkylene oxides, e.g. ethylene oxide, propylene oxide, 1,2-butylene oxide, 2,3-butylene oxide, 2-methyl-1,2-propene oxide (isobutene oxide), 1,2-pentene oxide, 2,3-pentene oxide, 2-methyl-1,2-butene oxide, 3-methyl-1,2-butene oxide, 1,2-hexene oxide, 2,3-hexene oxide, 3,4-hexene oxide, 2-methyl-1,2-pentene oxide, 2-ethyl-1,2-butene oxide, 3-methyl-1,2-pentene oxide, 1,2-decene oxide, 1,2-dodecene oxide or 4-methyl-1,2-pentene oxide, and also aromatic-substituted ethylene oxides such as optionally substituted styrene oxide, especially styrene oxide or 4-methylstyrene oxide.

In the case of use of epoxides as quaternizing agents, they are usually used in the presence of free acids, especially in the presence of free protic acids, such as in particular with $C_1$- to $C_{12}$-monocarboxylic acids, e.g. formic acid, acetic acid or propionic acid, or $C_2$- to $C_{12}$-dicarboxylic acids, e.g. oxalic acid or adipic acid, or else in the presence of sulfonic acids, e.g. benzenesulfonic acid or toluenesulfonic acid, or aqueous mineral acids, e.g. sulfuric acid or hydrochloric acid.

To perform the quaternization, the polytetrahydrobenzoxazine from reaction step (C) is admixed typically with at least one epoxide, especially in the stoichiometric amounts required to achieve the desired quaternization. Per equivalent of quaternizable tertiary nitrogen atom, it is possible to use, for example, 0.1 to 1.5 equivalents, or 0.5 to 1.25 equivalents, of quaternizing agent. More particularly, however, approximately equimolar proportions of the epoxide are used to quaternize a tertiary amine group. The temperatures employed here are typically in the range from 15 to 90° C., especially from 20 to 80° C. or from 30 to 70° C. The reaction time may be in the region of a few minutes or a few hours, for example about 10 minutes up to about 24 hours. The reaction can be effected at a pressure of about 0.1 to 20 bar, for example 1 to 10 or 1.5 to 3 bar, but especially at approximately standard pressure. More particularly, an inert gas atmosphere, for example nitrogen, is appropriate.

If required, the reactants can be initially charged in a suitable inert organic aliphatic or aromatic solvent or a mixture of such solvents for the quaternization, or a sufficient proportion of solvent from reaction step (C) is still present. Typical examples of suitable solvents are those of the abovementioned Solvesso™ series, and also toluene or xylene.

The present invention also provides a process for preparing polytetrahydrobenzoxazines, which comprises successively performing the reaction steps already described above, namely (A) reacting at least one diamine of the general formula $H_2N-A-NH_2$, in which the bridging member A is $C_1$- to $C_{20}$-alkylene which may be interrupted by up to 10 oxygen atoms and/or tertiary nitrogen atoms, $C_2$- to $C_{20}$-alkenylene, $C_5$- to $C_{20}$-cycloalkylene, $C_6$- to $C_{20}$-arylene or $C_7$- to $C_{20}$-aralkylene with at least one $C_1$- to $C_{12}$-aldehyde and at least one $C_1$- to $C_8$-alkanol at a temperature of 20 to 80° C. with elimination and removal of water, where both the aldehyde and the alcohol may be used in each case in more than double the molar amount compared to the diamine;

(B) reacting the condensation product from reaction step (A) with at least one phenol which bears at least one long-chain substituent having 6 to 3000 carbon atoms in a stoichiometric ratio to the diamine originally used in step (A) of 1.2:1 to 3.5:1 at a temperature of 30 to 120° C.;

(C) heating the reaction product from reaction step (B) to a temperature of 125 to 280° C. for at least 10 minutes.

In a preferred embodiment, a further characterizing feature of this process for preparing quaternized polytetrahydrobenzoxazines is that reaction steps (A), (B) and (C) and additionally the reaction step also already described in detail above, namely (D) quaternizing some or all quaternizable amino functions of the reaction product from reaction step (C), are performed successively.

The inventive polytetrahydrobenzoxazines can alternatively also be defined by their general chemical structure. Accordingly, the present invention provides polytetrahydrobenzoxazines of the general formula I

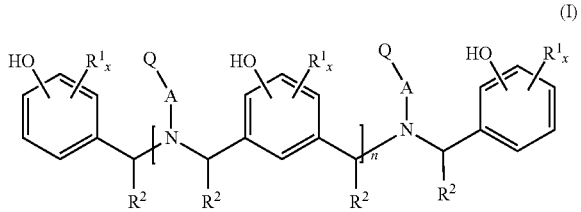

in which x is the number 1, 2, 3 or 4, where the values of x may be different on the different aromatic rings, n is an integer from 2 to 10, especially from 4 to 8, $R^1$ denotes identical or different $C_1$- to $C_{3000}$-hydrocarbyl radicals, where each benzene ring bears at least one $C_6$- to $C_{3000}$-hydrocarbyl radical, $R^2$ denotes hydrogen or identical or different $C_1$- to $C_{11}$-alkyl radicals, A is a bridging member having 2 to 20 carbon atoms and Q is the radical of a tetrahydrobenzoxazine unit which is attached via a nitrogen atom and which may be present in cyclic form according to the formula

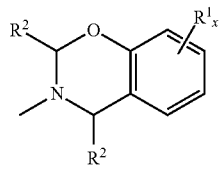

or in ring-opened form resulting from hydrolysis of the tetrahydrooxazine ring, where the variables $R^1$, $R^2$ and x are each as defined above. In this formula, $R^1$ are the substituents of the phenol used in the above-described reaction step (B), $R^2$ is the radical of the aldehyde used in the reaction step (A) described above, and A corresponds to the bridging member A in the general formula for the diamine $H_2N$-A-$NH_2$ used in the above-described reaction step (A).

Since the bistetrahydrobenzoxazines described, as intermediates and also as potential fuel and lubricant additives, are new compounds, the present invention likewise provides bistetrahydrobenzoxazines of the general formula II

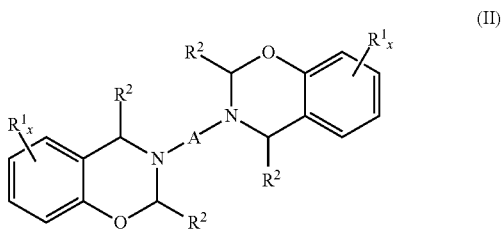

in which x is the number 1, 2, 3 or 4, where the values of x may be different on the two different aromatic rings, $R^1$ denotes identical or different $C_1$- to $C_{3000}$-hydrocarbyl radicals, where each benzene ring bears at least one $C_6$- to $C_{3000}$-hydrocarbyl radical, $R^2$ denotes hydrogen or identical or different $C_1$- to $C_{11}$-alkyl radicals, A is a bridging member having 2 to 20 carbon atoms, and ring-opened forms of the bistetrahydrobenzoxazines of the general formula II resulting from hydrolysis of one or both tetrahydrooxazine rings, where $R^1$ are the substitutents of the phenol used in the above-described reaction step (B), $R^2$ is the radical of the aldehyde used in the above-described reaction step (A), and A corresponds to the bridging member A in the general formula for the diamine $H_2N$-A-$NH_2$ used in the above-described reaction step (A).

The inventive polytetrahydrobenzoxazines and quaternized polytetrahydrobenzoxazines and the inventive bistetrahydrobenzoxazines are outstandingly suitable as fuel additives or lubricant additives. Fuels in which the inventive polytetrahydrobenzoxazines or quaternized polytetrahydrobenzoxazines or the inventive bistetrahydrobenzoxazines can be used as a fuel additive here are especially gasoline fuels and middle distillate fuels, and here in particular diesel fuels and heating oils.

To a very particular degree, the inventive polytetrahydrobenzoxazines and quaternized polytetrahydrobenzoxazines and the inventive bistetrahydrobenzoxazines are suitable as a detergent additive for diesel fuels.

Especially in their capacity as a detergent additive for diesel fuels, the inventive polytetrahydrobenzoxazines and quaternized polytetrahydrobenzoxazines and the inventive bistetrahydrobenzoxazines find use as an additive for reducing the level of or preventing deposits in injection systems of direct-injection diesel engines, especially in common-rail injection systems, for reducing fuel consumption of direct-injection diesel engines, especially of diesel engines with common-rail injection systems, and/or for minimizing power loss in direct-injection diesel engines, especially in diesel engines with common-rail injection systems.

The present invention also provides an additive concentrate which comprises, in combination with further fuel additives, especially diesel fuel additives, at least one inventive polytetrahydrobenzoxazine or quaternized polytetrahydrobenzoxazine, or an inventive bistetrahydrobenzoxazine.

The inventive polytetrahydrobenzoxazines or quaternized polytetrahydrobenzoxazine or the inventive bistetrahydrobenzoxazines are present in the inventive additive concentrate preferably in an amount of 0.1 to 100% by weight, more preferably of 1 to 80% by weight and especially of 10 to 70% by weight, based on the total weight of the concentrate.

The present invention further provides a fuel composition, especially a diesel fuel composition, which comprises, in a majority of a customary base fuel, especially of a diesel fuel, an effective amount of at least one inventive polytetrahydrobenzoxazine or quaternized polytetrahydrobenzoxazine or of an inventive bistetrahydrobenzoxazine.

The present invention further provides a lubricant composition, which comprises, in a majority of a customary lubricant formulation, an effective amount of at least one inventive polytetrahydrobenzoxazine or quaternized polytetrahydrobenzoxazine or of an inventive bistetrahydrobenzoxazine.

Useful gasoline fuels include all commercial gasoline fuel compositions. Typical representatives which shall be mentioned here include the market standard Eurosuper base fuel to EN 228. Further possible fields of use for the present invention are also gasoline fuel compositions of the specification according to WO 00/47698.

Useful middle distillate fuels include all commercial diesel fuel and heating oil compositions. Diesel fuels are typically mineral oil raffinates which generally have a boiling range of from 100 to 400° C. These are usually distillates having a 95% point up to 360° C. or even higher. However, they may also be so-called "Ultra low sulfur diesel" or "City diesel", characterized by a 95% point of, for example, not more than 345° C. and a sulfur content of not more than 0.005% by weight, or by a 95% point of, for example, 285° C. and a sulfur content of not more than 0.001% by weight. In addition to the diesel fuels obtainable by refining, whose main constituents are relatively long-chain paraffins, those obtainable by coal gasification or gas liquefaction ["gas to liquid" (GTL) fuels] are suitable. Also suitable are mixtures of the aforementioned diesel fuels with renewable fuels such as biodiesel or bioethanol. Of particular interest at the present time are diesel fuels with a low sulfur content, i.e. with a sulfur content of less than 0.05% by weight, preferably of less than 0.02% by weight, in particular of less than 0.005% by weight and especially of less than 0.001% by weight of sulfur. Diesel fuels may also comprise water, for example in an amount up to 20% by weight, for example in the form of diesel-water microemulsions or as so-called "white diesel".

Heating oils are, for example, low-sulfur or sulfur-rich mineral oil raffinates or bituminous coal or brown coal distillates which typically have a boiling range of from 150 to 400° C. Heating oils may be standard heating oil according to DIN 51603-1, which has a sulfur content of from 0.005 to 0.2% by weight, or they are low-sulfur heating oils having a sulfur content of from 0 to 0.005% by weight. Examples of heating oil include especially heating oil for domestic oil-fired boilers or EL heating oil.

The inventive polytetrahydrobenzoxazines or quaternized polytetrahydrobenzoxazines or the inventive bistetrahydrobenzoxazines can either be added to the particular base fuel, especially the gasoline or the diesel fuel, alone or in the form of fuel additive packages, for example the so-called diesel performance packages. Such packages are fuel additive concentrates and generally comprise, as well as solvents, also a series of further components as coadditives, for example carrier oils, cold flow improvers, corrosion inhibitors, demulsifiers, dehazers, antifoams, further cetane number improvers, further combustion improvers, antioxidants or stabilizers, antistats, metallocenes, metal deactivators, solubilizers, markers and/or dyes.

In a preferred embodiment, the additized gasoline or diesel fuel comprises, in addition to the inventive polytetrahydrobenzoxazines or quaternized polytetrahydrobenzoxazines or inventive bistetrahydrobenzoxazines, as further fuel additives, especially at least one (further) detergent additive, referred to hereinafter as component (D).

Detergents or detergent additives (D) typically refer to deposition inhibitors for fuels. The detergents are preferably amphiphilic substances which have at least one hydrophobic hydrocarbyl radical having a number-average molecular weight ($M_n$) of 85 to 20 000, especially of 300 to 5000 and in particular of 500 to 2500, and at least one polar moiety which is selected from (Da) mono- or polyamino groups having up to 6 nitrogen atoms, at least one nitrogen atom having basic properties;

(Db) nitro groups, optionally in combination with hydroxyl groups;

(Dc) hydroxyl groups in combination with mono- or polyamino groups, at least one nitrogen atom having basic properties;

(Dd) carboxyl groups or their alkali metal or alkaline earth metal salts;

(De) sulfo groups or their alkali metal or alkaline earth metal salts;

(Df) polyoxy-$C_2$-$C_4$-alkylene moieties terminated by hydroxyl groups, mono- or polyamino groups, at least one nitrogen atom having basic properties, or by carbamate groups;

(Dg) carboxylic ester groups;

(Dh) moieties derived from succinic anhydride and having hydroxyl and/or amino and/or amido and/or imido groups; and/or (Di) moieties obtained by Mannich reaction of substituted phenols with aldehydes and mono- or polyamines.

The hydrophobic hydrocarbon radical in the above detergent additives, which ensures the adequate solubility in the fuel oil composition, has a number-average molecular weight ($M_n$) of 85 to 20 000, especially of 300 to 5000, in particular of 500 to 2500. Useful typical hydrophobic hydrocarbyl radicals, especially in conjunction with the polar moieties (Da), (Dc), (Dh) and (Di), are relatively long-chain alkyl and alkenyl groups, especially the polypropenyl, polybutenyl and polyisobutenyl radicals each having $M_n$=300 to 5000, especially 500 to 2500, in particular 700 to 2300.

Examples of the above groups of detergent additives include the following:

Additives comprising mono- or polyamino groups (Da) are preferably polyalkenemono- or polyalkenepolyamines based on polypropene or conventional (i.e. having predominantly internal double bonds) polybutene or polyisobutene having $M_n$=300 to 5000. When the preparation of the additives proceeds from polybutene or polyisobutene having predominantly internal double bonds (usually in the β and γ positions), one possible preparative route is by chlorination and subsequent amination or by oxidation of the double bond with air or ozone to give the carbonyl or carboxyl compound and subsequent amination under reductive (hydrogenating) conditions. The amines used here for the amination may be, for example, ammonia, monoamines or polyamines such as dimethylaminopropylamine, ethylenediamine, diethylenetriamine, triethylenetetramine or tetraethylenepentamine. Corresponding additives based on polypropene are described in particular in WO-A-94/24231.

Further preferred additives comprising monoamino groups (Da) are the hydrogenation products of the reaction products of polyisobutenes having an average degree of polymerization P=5 to 100 with nitrogen oxides or mixtures of nitrogen oxides and oxygen, as described in particular in WO-A-97/03946.

Further preferred additives comprising monoamino groups (Da) are the compounds obtainable from polyisobutene epoxides by reaction with amines and subsequent dehydration and reduction of the amino alcohols, as described in particular in DE-A-196 20 262.

Additives comprising nitro groups (Db), optionally in combination with hydroxyl groups, are preferably reaction products of polyisobutenes having an average degree of polymerization P=5 to 100 or 10 to 100 with nitrogen oxides or mixtures of nitrogen oxides and oxygen, as described in particular in WO-A-96/03367 and in WO-A 96/03479. These reaction products are generally mixtures of pure nitropolyisobutenes (e.g. α,β-dinitropolyisobutene) and mixed hydroxynitropolyisobutenes (e.g. α-nitro-β-hydroxypolyisobutene).

Additives comprising hydroxyl groups in combination with mono- or polyamino groups (Dc) are in particular reaction products of polyisobutene epoxides obtainable from polyisobutene having preferably predominantly terminal double bonds and $M_n$=300 to 5000, with ammonia or mono- or polyamines, as described in particular in EP-A-476 485.

Additives comprising carboxyl groups or their alkali metal or alkaline earth metal salts (Dd) are preferably copolymers of $C_2$-$C_{40}$-olefins with maleic anhydride which have a total molar mass of 500 to 20 000 and some or all of whose carboxyl groups have been converted to the alkali metal or alkaline earth metal salts and any remainder of the carboxyl groups has been reacted with alcohols or amines. Such additives are disclosed in particular by EP-A-307 815. Such additives serve mainly to prevent valve seat wear and can, as described in WO-A-87/01126, advantageously be used in combination with customary fuel detergents such as poly(iso) buteneamines or polyetheramines.

Additives comprising sulfo groups or their alkali metal or alkaline earth metal salts (De) are preferably alkali metal or alkaline earth metal salts of an alkyl sulfosuccinate, as described in particular in EP-A-639 632. Such additives serve mainly to prevent valve seat wear and can be used advantageously in combination with customary fuel detergents such as poly(iso)buteneamines or polyetheramines.

Additives comprising polyoxy-$C_2$-$C_4$-alkylene moieties (Df) are preferably polyethers or polyetheramines which are obtainable by reaction of $C_2$-$C_{60}$-alkanols, $C_6$-$C_{30}$-alkanediols, mono- or di-$C_2$-$C_{30}$-alkylamines, $C_1$-$C_{30}$-alkylcyclohexanols or $C_1$-$C_{30}$-alkylphenols with 1 to 30 mol of ethylene oxide and/or propylene oxide and/or butylene oxide per hydroxyl group or amino group and, in the case of the polyetheramines, by subsequent reductive amination with ammonia, monoamines or polyamines. Such products are described in particular in EP-A-310 875, EP-A-356 725, EP-A-700 985 and U.S. Pat. No. 4,877,416. In the case of polyethers, such products also have carrier oil properties. Typical examples of these are tridecanol butoxylates, isotridecanol butoxylates, isononylphenol butoxylates and polyisobutenol butoxylates and propoxylates and also the corresponding reaction products with ammonia.

Additives comprising carboxylic ester groups (Dg) are preferably esters of mono-, di- or tricarboxylic acids with long-chain alkanols or polyols, in particular those having a minimum viscosity of 2 mm$^2$/s at 100° C., as described in particular in DE-A-38 38 918. The mono-, di- or tricarboxylic acids used may be aliphatic or aromatic acids, and particularly suitable ester alcohols or ester polyols are long-chain representatives having, for example, 6 to 24 carbon atoms. Typical representatives of the esters are adipates, phthalates, isophthalates, terephthalates and trimellitates of isooctanol, of isononanol, of isodecanol and of isotridecanol. Such products also have carrier oil properties.

Additives comprising moieties derived from succinic anhydride and having hydroxyl and/or amino and/or amido and/or imido groups (Dh) are preferably corresponding derivatives of alkyl- or alkenyl-substituted succinic anhydride and especially the corresponding derivatives of polyisobutenylsuccinic anhydride which are obtainable by reacting conventional or high-reactivity polyisobutene having $M_n$=300 to 5000 with maleic anhydride by a thermal route or via the chlorinated polyisobutene. Of particular interest in this context are derivatives with aliphatic polyamines such as especially ethylenediamine, diethylenetriamine, triethylenetetramine or tetraethylenepentamine. The moieties having hydroxyl and/or amino and/or amido and/or imido groups are, for example, carboxylic acid groups, acid amides of monoamines, acid amides of di- or polyamines which, in addition to the amide function, also have free amine groups, succinic acid derivatives having an acid and an amide function, carboximides with monoamines, carboximides with di- or polyamines which, in addition to the imide function, also have free amine groups, or diimides which are formed by the reaction of di- or polyamines with two succinic acid derivatives. Such fuel additives are common knowledge and are described especially in U.S. Pat. No. 4,849,572.

The detergent additives from group (Dh) are preferably the reaction products of alkyl- or alkenyl-substituted succinic anhydrides, especially of polyisobutenylsuccinic anhydrides, with amines and/or alcohols. These are thus derivatives which are derived from alkyl-, alkenyl- or polyisobutenylsuccinic anhydride and have amino and/or amido and/or imido and/or hydroxyl groups. It is self-evident that these reaction products are obtainable not only when substituted succinic anhydride is used, but also when substituted succinic acid or suitable acid derivatives, such as succinyl halides or succinic esters, are used.

The additized fuel preferably comprises at least one detergent based on a polyisobutenyl-substituted succinimide. Especially of interest are the imides with aliphatic polyamines. Particularly preferred polyamines are ethylenediamine, diethylenetriamine, triethylenetetramine, pentaethylenehexamine and in particular tetraethylenepentamine. The polyisobutenyl radical has a number-average molecular weight $M_n$ of preferably from 500 to 5000, more preferably from 500 to 2000 and in particular of about 1000.

Additives comprising moieties (Di) obtained by Mannich reaction of substituted phenols with aldehydes and mono- or polyamines are preferably reaction products of polyisobutene-substituted phenols with formaldehyde and mono- or polyamines such as ethylenediamine, diethylenetriamine, triethylenetetramine, tetraethylenepentamine or dimethylaminopropylamine. The polyisobutenyl-substituted phenols may originate from conventional or high-reactivity polyisobutene having $M_n$=300 to 5000. Such "polyisobutene Mannich bases" are described especially in EP-A-831 141.

The detergent additives (D) mentioned are preferably used together with the inventive polytetrahydrobenzoxazines or quaternized polytetrahydrobenzoxazines or the inventive bistetrahydrobenzoxazines in combination with at least one carrier oil.

Suitable mineral carrier oils are the fractions obtained in crude oil processing, such as brightstock or base oils having viscosities, for example, from the SN 500-2000 class; but also aromatic hydrocarbons, paraffinic hydrocarbons and alkoxyalkanols. Likewise useful is a fraction which is obtained in the refining of mineral oil and is known as "hydrocrack oil" (vacuum distillate cut having a boiling range of from about 360 to 500° C., obtainable from natural mineral oil which has been catalytically hydrogenated under high pressure and isomerized and also deparaffinized). Likewise suitable are mixtures of abovementioned mineral carrier oils.

Examples of suitable synthetic carrier oils are selected from: polyolefins (poly-alpha-olefins or poly(internal olefin)s), (poly)esters, (poly)alkoxylates, polyethers, aliphatic polyetheramines, alkylphenol-started polyethers, alkylphenol-started polyetheramines and carboxylic esters of long-chain alkanols.

Examples of suitable polyolefins are olefin polymers having $M_n$=from 400 to 1800, in particular based on polybutene or polyisobutene (hydrogenated or unhydrogenated).

Examples of suitable polyethers or polyetheramines are preferably compounds comprising polyoxy-$C_2$-$C_4$-alkylene moieties which are obtainable by reacting $C_2$-$C_{60}$-alkanols, $C_6$-$C_{30}$-alkanediols, mono- or di-$C_2$-$C_{30}$-alkylamines, $C_1$-$C_{30}$-alkylcyclohexanols or $C_1$-$C_{30}$-alkylphenols with from 1 to 30 mol of ethylene oxide and/or propylene oxide and/or butylene oxide per hydroxyl group or amino group, and, in the case of the polyetheramines, by subsequent reductive amination with ammonia, monoamines or polyamines. Such products are described in particular in EP-A 310 875, EP-A 356 725, EP-A 700 985 and U.S. Pat. No. 4,877,416. For example, the polyetheramines used may be poly-$C_2$-$C_6$-alkylene oxide amines or functional derivatives thereof. Typical examples thereof are tridecanol butoxylates or isotridecanol butoxylates, isononylphenol butoxylates and also polyisobutenol butoxylates and propoxylates, and also the corresponding reaction products with ammonia.

Examples of carboxylic esters of long-chain alkanols are in particular esters of mono-, di- or tricarboxylic acids with long-chain alkanols or polyols, as described in particular in DE-A 38 38 918. The mono-, di- or tricarboxylic acids used may be aliphatic or aromatic acids; suitable ester alcohols or polyols are in particular long-chain representatives having, for example, from 6 to 24 carbon atoms. Typical representatives of the esters are adipates, phthalates, isophthalates, terephthalates and trimellitates of isooctanol, isononanol, isodecanol and isotridecanol, for example di(n- or isotridecyl) phthalate.

Further suitable carrier oil systems are described, for example, in DE-A 38 26 608, DE-A 41 42 241, DE-A 43 09 074, EP-A 0 452 328 and EP-A 0 548 617.

Examples of particularly suitable synthetic carrier oils are alcohol-started polyethers having from about 5 to 35, for example from about 5 to 30, $C_3$-$C_6$-alkylene oxide units, for example selected from propylene oxide, n-butylene oxide and isobutylene oxide units, or mixtures thereof. Nonlimiting examples of suitable starter alcohols are long-chain alkanols or phenols substituted by long-chain alkyl in which the long-chain alkyl radical is in particular a straight-chain or branched $C_6$-$C_{18}$-alkyl radical. Preferred examples include tridecanol and nonylphenol.

Further suitable synthetic carrier oils are alkoxylated alkylphenols, as described in DE-A 101 02 913.

Preferred carrier oils are synthetic carrier oils, particular preference being given to polyethers.

The inventive fuel composition comprises the inventive polytetrahydrobenzoxazines or quaternized polytetrahydrobenzoxazines or the inventive bistetrahydrobenzoxazines in an amount of typically 10 to 2000 ppm by weight, more preferably of 20 to 1000 ppm by weight, even more preferably of 30 to 500 ppm by weight and especially of 40 to 200 ppm by weight, z. B. von 50 to 150 ppm by weight.

When the inventive polytetrahydrobenzoxazines or quaternized polytetrahydrobenzoxazines or the inventive bistetrahydrobenzoxazines are added to the fuel in combination with one or more (further) detergent additives from group (D), the total amount of these two additive types is typically 10 to 3000 ppm by weight, more preferably from 20 to 1500 ppm by weight, even more preferably from 30 to 1000 ppm by weight and especially from 40 to 500 ppm by weight, for example from 50 to 300 ppm by weight.

When a carrier oil is used in addition, it is added to the inventive additized fuel in an amount of preferably from 1 to 1000 ppm by weight, more preferably from 10 to 500 ppm by weight and in particular from 20 to 100 ppm by weight.

Cold flow improvers suitable as further coadditives are, for example, copolymers of ethylene with at least one further unsaturated monomer, e.g. ethylene-vinyl acetate copolymers.

Corrosion inhibitors suitable as further coadditives are, for example, succinic esters, in particular with polyols, fatty acid derivatives, for example oleic esters, oligomerized fatty acids and substituted ethanolamines.

Demulsifiers suitable as further coadditives are, for example, the alkali metal and alkaline earth metal salts of alkyl-substituted phenol- and naphthalenesulfonates and the alkali metal and alkaline earth metal salts of fatty acid, and also alcohol alkoxylates, e.g. alcohol ethoxylates, phenol alkoxylates, e.g. tert-butylphenol ethoxylates or tert-pentylphenol ethoxylates, fatty acid, alkylphenols, condensation products of ethylene oxide and propylene oxide, e.g. ethylene oxide-propylene oxide block copolymers, polyethyleneimines and polysiloxanes.

Dehazers suitable as further coadditives are, for example, alkoxylated phenol-formaldehyde condensates.

Antifoams suitable as further coadditives are, for example, polyether-modified polysiloxanes.

Cetane number and combustion improvers suitable as further coadditives are, for example, alkyl nitrates, e.g. cyclohexyl nitrate and especially 2-ethylhexyl nitrate, and peroxides, e.g. di-tert-butyl peroxide.

Antioxidants suitable as further coadditives are, for example, substituted phenols, e.g. 2,6-di-tert-butylphenol and 2,6-di-tert-butyl-3-methylphenol, and also phenylenediamines, e.g. N,N'-di-sec-butyl-p-phenylenediamine.

Metal deactivators suitable as further coadditives are, for example, salicylic acid derivatives, e.g. N,N'-disalicylidene-1,2-propanediamine.

Suitable solvents, especially for fuel additive packages, are, for example, nonpolar organic solvents, especially aromatic and aliphatic hydrocarbons, for example toluene, xylenes, "white spirit" and the technical solvent mixtures of the designations Shellsol® (manufacturer: Royal Dutch/Shell Group), Exxol® (manufacturer: ExxonMobil) and Solvent Naphtha. Also useful here, especially in a blend with the nonpolar organic solvents mentioned, are polar organic solvents, in particular alcohols such as 2-ethylhexanol, decanol and isotridecanol.

When the coadditives and/or solvents mentioned are used in addition in gasoline or diesel fuel, they are used in the amounts customary therefor.

The inventive polytetrahydrobenzoxazines and quaternized polytetrahydrobenzoxazines and the inventive bistetrahydrobenzoxazines are also particularly advantageously suitable as a lubricant additive. Lubricants or lubricant compositions are intended to refer here to motor oil, lubricant oils, transmission oils including manual and automatic oils, and related liquid compositions which serve to lubricate mechanically moving parts—usually in metal form. The inventive polytetrahydrobenzoxazines and quaternized polytetrahydrobenzoxazines and the inventive bistetrahydrobenzoxazines act principally as dispersant additive and/or as detergent additive in the lubricant compositions.

The inventive lubricant composition comprises the inventive polytetrahydrobenzoxazines or quaternized polytetrahydrobenzoxazines or the inventive bistetrahydrobenzoxazines in an amount of typically 0.001 to 20% by weight, preferably 0.01 to 10% by weight, especially 0.05 to 8% by weight and in particular 0.1 to 5% by weight, based on the total amount of the lubricant composition.

The economically most important lubricant compositions are motor oils, and also transmission oils including manual and automatic oils. Motor oils consist typically of mineral base oils which comprise predominantly paraffinic constituents and are produced in the refinery by costly inconvenient workup and purification processes, having a fraction of approx. 2 to 10% by weight of additives (based on the active substance contents). For specific applications, for example high-temperature applications, the mineral base oils may be replaced partly or fully by synthetic components such as organic esters, synthetic hydrocarbons such as olefin oligomers, poly-α-olefins or polyolefins of hydrocracking oils. Motor oils also have to have sufficiently high viscosities at high temperatures in order to ensure impeccable lubrication effect and good sealing between cylinder and piston. Moreover, the flow properties of motor oils have to be such that the engine can be started without any problem at low temperatures. Motor oils have to be oxidation-stable and must generate only small amounts of decomposition products in liquid or solid form and deposits even under difficult working conditions. Motor oils disperse solids (dispersant behavior), prevent deposits (detergent behavior), neutralize acidic reaction products and form a wear protective film on the metal surfaces in the engine. Motor oils are typically characterized by viscosity classes (SAE classes).

With regard to their base components and additives, transmission oils including manual and automatic oils have a similar composition to motor oils. The force is transmitted in the gear system of gearboxes to a high degree through the liquid pressure in the transmission oil between the teeth. The transmission oil accordingly has to be such that it withstands high pressures for prolonged periods without decomposing. In addition to the viscosity properties, wear, pressure resistance, friction, shear stability, traction and running-in performance are the crucial parameters here.

In addition to the inventive polytetrahydrobenzoxazines or quaternized polytetrahydrobenzoxazines or the inventive bistetrahydrobenzoxazines, motor oils and transmission oils including manual and automatic oils generally also comprise at least one, but usually some or all, of the additives listed below in the amounts customary therefor (which are stated in brackets in % by weight, based on the overall lubricant composition):

antioxidants (0.1 to 5%):
sulfur compounds, for example reaction products of terpenes (α-pinene), resin oils or low molecular weight polybutenes with sulfur, dialkyl sulfides, dialkyl trisulfides, polysulfides, diaryl sulfides, modified thiols, mercaptobenzimidazoles, mercaptotriazines, thiophene derivatives, xanthates, zinc dialkyldithiocarbamates, thioglycols, thioaldehydes, dibenzyl disulfide, alkylphenol sulfides, dialkylphenol sulfides or sulfur-containing carboxylic acids phosphorus compounds, for example triaryl and trialkyl phosphites, dialkyl 3,5-di-tert-butyl-4-hydroxybenzylphosphonate or phosphonic acid piperazides sulfur-phosphorus compounds, for example zinc dialkyldithiophosphates (metal dialkyldithiophosphates also act as corrosion inhibitors and high-pressure additives in lubricant oils) or reaction products of phosphorus pentasulfide with terpenes (α-pinene, dipentene), polybutenes, olefins or unsaturated esters phenol derivatives, for example sterically hindered mono-, bis- or trisphenols, sterically hindered polycyclic phenols, polyalkylphenols, 2,6-di-tert-butyl-4-methylphenol or methylene-4,4'-bis(2,6-di-tert-butylphenol) (phenol derivatives are often used in combination with sulfur-based or amine-based antioxidants)

amines, for example arylamines such as diphenylamine, phenyl-α-naphthylamine or 4,4'-tetramethyldiaminodiphenylmethane metal deactivators in the narrower sense, for example N-salicylideneethylamine, N,N'-disalicylideneethylenediamine, N,N'-disalicylidene-1,2-propanediamine, triethylenediamine, ethylenediaminetetraacetic acid, phosphoric acid, citric acid, glycolic acid, lecithin, thiadiazole, imidazole or pyrazole derivatives viscosity index improvers (0.05 to 10%), for example: polyisobutenes having a molecular weight of typically 10 000 to 45 000, polymethacrylates having a molecular weight of typically 15 000 to 100 000, homo- and copolymers of 1,3-dienes such as butadiene or isoprene having a molecular weight of typically 80 000 to 100 000, 1,3-diene-styrene copolymers having a molecular weight of typically 80 000 to 100 000, maleic anhydride-styrene polymers in esterified form having a molecular weight of typically 60 000 to 120 000, star-shaped polymers with block-like structure by virtue of units composed of conjugated dienes and aromatic monomers having a molecular weight of typically 200 000 to 500 000, polyalkylstyrenes having a molecular weight of typically 80 000 to 150 000, polyolefins composed of ethylene and propylene or styrene-cyclopentadiene-norbornene terpolymers having a molecular weight of typically 60 000 to 140 000 pour point depressants (cold flow improvers) (0.03 to 1%), for example bicyclic aromatics such as naphthalene with different long-chain alkyl radicals, polymethacrylates with 12 to 18 carbon atoms in the alcohol radical, a degree of branching between 10 to 30 mol % and an average molecular weight of 5000 to 500 000, long-chain alkylphenols and dialkylaryl phthalates or copolymers of different olefins detergents (HD additives) (0.2 to 4%), for example calcium naphthenates, lead naphthenates, zinc naphthenates and manganese naphthenates, calcium dichlorostearates, calcium phenylstearates, calcium chlorophenylstearates, sulfonation products of alkylaromatics such as dodecylbenzene, petroleum sulfonates, sodium sulfonates, calcium sulfonates, barium sulfonates or magnesium sulfonates, neutral, basic and overbased sulfonates, phenates and carboxylates, salicylates, metal salts of alkylphenols and alkylphenol sulfides, phosphates, thiophosphates or alkenylphosphonic acid derivatives ashless dispersants (0.5 to 10%), for example Mannich condensates of alkylphenol, formaldehyde and poly-alkylenepolyamines, reaction products of polyisobutenylsuccinic anhydrides with polyhydroxyl compounds or polyamines, copolymers of alkyl methacrylates with diethylaminoethyl methacrylate, N-vinylpyrrolidone, N-vinylpyridine or 2-hydroxyethyl methacrylate or vinyl acetate-fumarate copolymers high-pressure additives (extreme pressure additives) (0.2 to 2.5%), for example chlorinated paraffins with chlorine content 40 to 70% by weight, chlorinated fatty acid (especially having trichloromethyl end groups), dialkyl hydrogenphosphites, triaryl phosphites, aryl phosphates such as tricresyl phosphate, dialkyl phosphates, trialkyl phosphates such as tributyl phosphate, trialkylphosphines, diphosphoric esters, nitroaromatics, aminophenol derivatives of naphthenic acid, carbamic esters, dithiocarbamic acid derivatives, substituted 1,2,3-triazoles, mixtures of benzotriazole and alkylsuccinic anhydride or alkylmaleic anhydride, 1,2,4-thiadiazole polymers, morpholinobenzothiadiazole disulfide, chlorinated alkyl sulfides, sulfurized olefins, sulfurized chloronaphthalenes, chlorinated alkyl thiocarbonates, organic sulfides and polysulfides such as bis(4-chlorobenzyl) disulfide and tetrachlorodiphenyl sulfide, trichloroacrolein mercaptals or especially zinc dialkyldithiophosphates (ZDDPs)

friction modifiers (0.05 to 1%), especially polar oil-soluble compounds which generate a thin layer on the frictional surface by adsorption, for example fatty alcohols, fatty amides, fatty acid salts, fatty acid alkyl esters or fatty acid glycerides antifoam additives (0.0001 to 0.2%), for example liquid silicones such as polydimethylsiloxanes or polyethylene glycol ethers and sulfides demulsifiers (0.1 to 1%), for example dinonylnaphthalenesulfonates in the form of their alkali metal and alkaline earth metal salts corrosion inhibitors (also known as metal deactivators) (0.01 to 2%), for example tertiary amines and salts thereof, imino esters, amide oximes, diaminomethanes, derivatives of saturated or unsaturated fatty acids with alkanolamines, alkylamines, sarcosines, imidazolines, alkylbenzotriazoles, dimercaptothiadiazole derivatives, diaryl phosphates, thiophosphoric esters, neutral salts of primary n-$C_8$-$C_{18}$-alkylamines or cycloalkylamines with dialkyl phosphates having branched $C_5$-$C_{12}$-alkyl groups, neutral or basic alkaline earth metal sulfonates, zinc naphthenates, mono- and dialkylarylsulfonates, barium dinonylnaphthalenesulfonates, lanolin (wool fat), heavy metal salts of naphthenic acid, dicarboxylic acid, unsaturated fatty acids, hydroxy fatty acids, fatty acid esters, pentaerythrityl monooleates and sorbitan monooleates, O-stearoylalkanolamines, polyisobutenylsuccinic acid derivatives or zinc dialkyldithiophosphates and zinc dialkyldithiocarbamates emulsifiers (0.01 to 1%), for example long-chain unsaturated, naturally occurring carboxylic acid, naphthenic acids, synthetic carboxylic acid, sulfonamides, N-oleylsarcosine, alkanesulfamidoacetic acid, dodecylbenzenesulfonate, long-chain alkylated ammonium salts such as dimethyldodecylbenzylammonium chloride, imidazolinium salts, alkyl-, alkylaryl-, acyl-, alkylamino- and acylaminopolyglycols or long-chain acylated mono- and diethanolamines dyes and fluorescence additives (0.001 to 0.2%)

preservatives (0.001 to 0.5%)

odor improvers (0.001 to 0.2%).

Typical ready-to-use motor oil compositions and transmission oil, including manual and automatic oil, compositions in the context of the present invention have the following composition, the data for the additives relating to the active substance contents and the sum of all components always adding up to 100% by weight:

80 to 99.3% by weight, in particular 90 to 98% by weight of motor oil base or transmission oil, including manual and automatic oil, base (mineral base oils and/or synthetic components) including the fractions of solvent and diluent for the additives 0.1 to 8% by weight of inventive polytetrahydrobenzoxazines or quaternized polytetrahydrobenzoxazines or the inventive bistetrahydrobenzoxazines 0.2 to 4% by weight, in particular 1.3 to 2.5% by weight of detergents of group (d)

0.5 to 10% by weight, in particular 1.3 to 6.5% by weight of dispersants of group (e)

0.1 to 5% by weight, in particular 0.4 to 2.0% by weight of antioxidants of group (a) and/or high-pressure additives of group (f) and/or friction modifiers of group (g)

0.05 to 10% by weight, in particular 0.2 to 1.0% by weight of viscosity index improvers of group (b)

0 to 2% by weight of other additives of groups (c) and (h) to (n).

The invention will be illustrated in detail with reference to the nonrestrictive examples which follow.

PREPARATION EXAMPLES

Example 1

Reaction Step (A)

250 g (3.37 mol) of isobutanol and 60 g (2.0 mol) of paraformaldehyde were suspended at 20° C. in 250 g of cyclohexane. This was followed by the addition of 30 g (0.50 mol) of 1,2-ethylenediamin. The reaction mixture was heated under reflux at 40° C. under a reduced pressure of 83 mbar for 5 hours. Water eliminated was removed azeotropically from the reaction mixture. A conversion of 75% was determined from the amount of water eliminated. After the cyclohexane solvent and the excess isobutanol had been distilled off, a product mixture comprising compounds IIIa, IIIb and IIIc (in a weight ratio of 1:0.7:0.4) as main products was obtained:

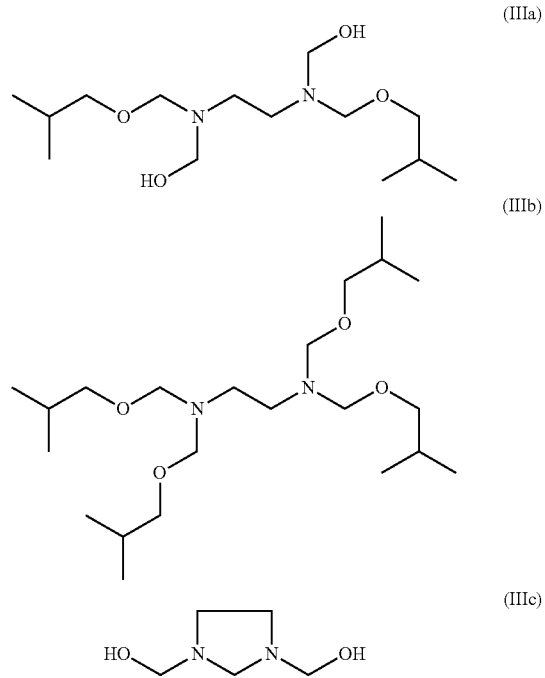

Also present in minor amounts in this product mixture are the corresponding tetrakis-(hydroxymethyl)ethylenediamine etherified with isobutanol on only one hydroxymethyl moiety, and the corresponding tris(hydroxymethyl)ethylenediamine etherified with isobutanol on only one hydroxymethyl moiety.

This product mixture shows, in the $^1$H NMR spectrum (CDCl$_3$, δ in ppm) the following significant signals:

for IIIa: 0.9 (m, —CH$_3$), 1.83 (m, —C$\underline{H}$—(CH$_3$)$_2$), 2.9 (s, —NCH$_2$CH$_2$N—), 3.25 (d, —OCH$_2$—) and 4.18 (s, —NCH$_2$O—);

for IIIb: 0.9 (m, —CH$_3$), 1.83 (m, —C$\underline{H}$—(CH$_3$)$_2$), 3.0 (s, —NCH$_2$CH$_2$N—), 3.25 (d, —OCH$_2$—) and 4.3 (s, —NCH$_2$O—);

for IIIc: 3.7 (s, —NCH$_2$CH$_2$N—) and 3.8 (s, —NCH$_2$N—).

Example 2

Reaction Step (B)

The product mixture prepared in example 1 was dissolved together with 262 g (1.0 mol) of 4-n-dodecylphenol in 525 g of Solvesso™ 150, and heated to 90° C. for 2 hours. Subsequently, the solvent was distilled off under reduced pressure. The result was a bistetrahydrobenzoxazine of the formula IIa (R$^1$=n-dodecyl) which had, in the $^1$H NMR spectrum (CDCl$_3$, δ in ppm), the following signals:

0.5-1.6 (m, —(CH$_2$)$_{11}$CH$_3$), 3.0 (s, —NCH$_2$CH$_2$N—), 4.0 (s, —NCH$_2$—), 4.9 (s, —OCH$_2$N—), 6.7 (s, aromat. CH, meta position), 6.8 and 7.0 (d, aromat. CH, ortho and meta position).

Example 3

Reaction Step (B)

The product mixture prepared in example 1 was dissolved together with 265 g (1.28 mol) of 4-tert-octylphenol in 520 g of toluene, and heated to 40° C. for 2 hours. Subsequently, the solvent was distilled off under reduced pressure. The result was a bistetrahydrobenzoxazine of the formula IIa (R$^1$=n-tert-octyl) which had, in the $^1$H NMR spectrum (CDCl$_3$, δ in ppm), the following signals:

1.3 (s, CH$_3$), 1.7 (s, —CH$_2$—), 3.0 (s, —NCH$_2$CH$_2$N—), 4.0 (s, —NCH$_2$—), 4.9 (s, —OCH$_2$N—), 6.9 (s, aromat. CH, meta position), 7.1-7.3 (m, aromat. CH, ortho and meta position).

Example 4

Reaction Step (B)

The product mixture prepared in example 1 was dissolved together with 281 g (1.29 mol) of 4-n-nonylphenol in 520 g toluene, and heated to 40° C. for 2 hours. Subsequently, the solvent was distilled off under reduced pressure. The result was a bistetrahydrobenzoxazine of the formula IIa (R$^1$=n-nonyl) which had, in the $^1$H NMR spectrum (CDCl$_3$, δ in ppm), the following signals:

0.5-1.7 (m, —(CH$_2$)$_8$CH$_3$), 3.0 (s, —NCH$_2$CH$_2$N—), 4.0 (s, —NCH$_2$—), 4.9 (s, —OCH$_2$N—), 6.7 (s, aromat. CH, meta position), 6.8 and 7.0 (d, aromat. CH, ortho and meta position).

Example 5

Reaction Step (C)

The bistetrahydrobenzoxazine from example 2 was dissolved in a weight ratio of 1:1 in Solvesso™ 150, and heated to 205° C. for 1 hour. After the solvent had been distilled off under reduced pressure, the result was a polytetrahydrobenzoxazine of the formula Ia (R$^1$=n-dodecyl, n=approx. 6), which had a number-average molecular weight (M$_w$) of 4600 g/mol, a number-average molecular weight (M$_n$) of 1500 g/mol and a polydispersity index (PDI) of 3.07, and exhibited the following signals in the $^1$H NMR spectrum (CDCl$_3$, δ in ppm):

0.5-1.6 (m, —(CH$_2$)$_{11}$CH$_3$), 3.0 (s, —NCH$_2$CH$_2$N—), 4.0 (s, —NCH$_2$—), 4.9 (s, —OCH$_2$N—), 6.7 (s, aromat. CH, meta position), 6.8 and 7.0 (d, aromat. CH, meta and ortho position).

Use Example

To examine the influence of the compounds described on the performance of direct-injection diesel engines operated with the inventive fuel composition, the power loss was determined based on the official test method CEC F-98-08. The power loss is a direct measure of formation of deposits in the injectors.

A conventional direct-injection diesel engine with a common-rail system was used. For more economical execution of the determinations, a shortened engine run cycle was used compared to CEC F-98-08, i.e. 1×12 hours of run time compared to 4×8 hours of run time interrupted by 3×8 hours of soak time of the original test method. In addition, injectors which had already been run in and cleaned were used. All other test details were fulfilled as in CEC F-98-08.

The fuel used was a commercial diesel fuel from Haltermann (RF-06-03 Batch 12). To synthetically induce the formation of deposits on the injectors, 2 ppm by weight of zinc didodecanoate were added thereto.

The additive used was the compound from example 5.

The table which follows shows the results of the power loss determinations:

| Test run No. | Detergent additive | Dosage [ppm by weight of active substance] | Power loss, 12 h [at 4000 rpm] |
|---|---|---|---|
| Base value | none | — | 4.34% |
| 1 | Example 5 | 150 | 0.41% |
| 2 | Example 5 | 150 | 0.71% |

The invention claimed is:

1. A bistetrahydrobenzoxazine of formula (II):

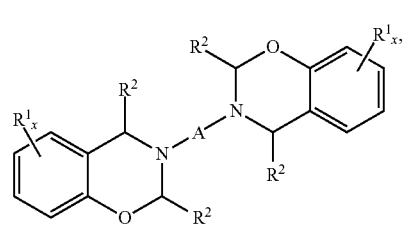

(II)

wherein:

x is independently 1, 2, 3 or 4;

R$^1$ is independently a C$_1$- to C$_{3000}$-hydrocarbyl radical, with the proviso that each benzene ring of the bistetrahydrobenzoxazine is substituted with at least one polyisobutyl radical comprising 21 to 1000 carbon atoms and each benzene ring is optionally further substituted with at least one C$_1$- to C$_{3000}$-hydrocarbyl radical;

$R^2$ is a hydrogen or independently a $C_1$- to $C_{11}$-alkyl radical; and

A is a bridging member having 1 to 20 carbon atoms, and ring-opened forms of the bistetrahydrobenzoxazine of formula (II) resulting from hydrolysis of one or both tetrahydrooxazine rings.

2. The bistetrahydrobenzoxazine compound of claim 1, having the formula (IIa):

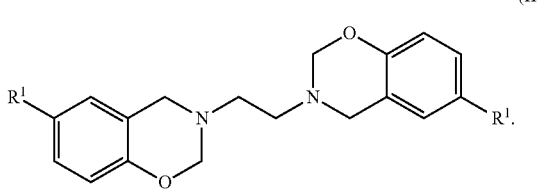

(IIa)

3. The bistetrahydrobenzoxazine compound of claim 1, wherein at least one benzene ring of the bistetrahydrobenzoxazine is further substituted with at least one additional $R^1$ selected from the group consisting of tert-octyl, n-nonyl and n-dodecyl.

4. The bistetrahydrobenzoxazine compound of claim 1, wherein A has 2 to 20 carbon atoms.

5. The bistetrahydrobenzoxazine compound of claim 1, wherein at least one x is 1.

6. The bistetrahydrobenzoxazine compound of claim 1, wherein at least one x is 2.

7. The bistetrahydrobenzoxazine compound of claim 1, wherein at least one x is 3.

8. The bistetrahydrobenzoxazine compound of claim 1, wherein at least one x is 4.

9. The bistetrahydrobenzoxazine compound of claim 1, wherein $R^2$ is hydrogen.

10. The bistetrahydrobenzoxazine compound of claim 1, wherein $R^2$ is independently a $C_1$- to $C_{11}$-alkyl radical.

11. A method of reducing or preventing deposits in an injection system of a direct-injection diesel engine for reducing fuel consumption of a direct-injection diesel engine and/or for minimizing power loss in a direct-injection diesel engine, the method comprising adding a bistetrahydrobenzoxazine to a fuel of the direct-injection diesel engine,
wherein the bistetrahydrobenzoxazine is a bistetrahydrobenzoxazine of formula (II):

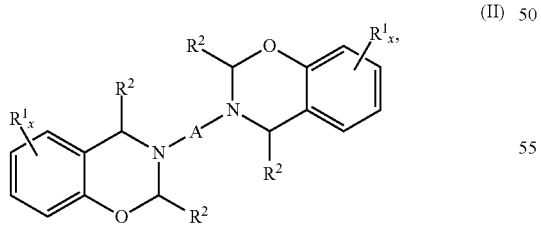

(II)

in which:

x is independently 1, 2, 3 or 4;

$R^1$ is independently a $C_1$- to $C_{3000}$-hydrocarbyl radical, with the proviso that each benzene ring of the bistetrahydrobenzoxazine is substituted with at least one polyisobutyl radical comprising 21 to 1000 carbon atoms and each benzene ring is optionally further substituted with at least one $C_1$- to $C_{3000}$-hydrocarbyl radical;

$R^2$ is a hydrogen or independently a $C_1$- to $C_{11}$-alkyl radical; and

A is a bridging member having 1 to 20 carbon atoms, and ring-opened forms of the bistetrahydrobenzoxazine of formula (II) resulting from hydrolysis of one or both tetrahydrooxazine rings.

12. The method of claim 11, wherein the direct-injection diesel engine comprises a common-rail injection system.

13. A fuel composition, comprising a base fuel and a bistetrahydrobenzoxazine of formula (II):

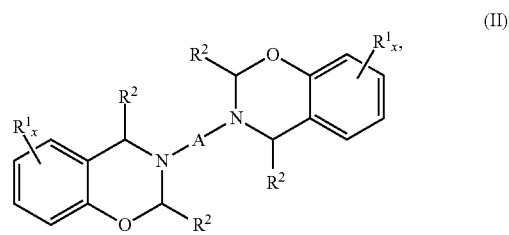

(II)

wherein:

x is independently 1, 2, 3 or 4;

$R^1$ is independently a $C_1$- to $C_{3000}$-hydrocarbyl radical, with the proviso that each benzene ring of the bistetrahydrobenzoxazine is substituted with at least one polyisobutyl radical comprising 21 to 1000 carbon atoms and each benzene ring is optionally further substituted with at least one $C_1$- to $C_{3000}$-hydrocarbyl radical;

$R^2$ is a hydrogen or independently a $C_1$- to $C_{11}$-alkyl radical; and

A is a bridging member having 1 to 20 carbon atoms, and ring-opened forms of the bistetrahydrobenzoxazine of formula (II) resulting from hydrolysis of one or both tetrahydrooxazine rings.

14. The fuel composition of claim 13, further comprising at least one co-additive and optionally at least one solvent.

15. The fuel composition of claim 13, wherein the base fuel is a gasoline or a diesel fuel.

16. The fuel composition of claim 14, wherein the co-additive is at least one selected from the group consisting of a carrier oil, a cold flow improver, a corrosion inhibitor, a demulsifier, a dehazer, an antifoam, a cetane number improver, a combustion improver, an antioxidant, a stabilizer, an antistat, a metallocene, a metal deactivator, a solubilizer, a marker and a dye.

\* \* \* \* \*